(12) United States Patent
Spatholt et al.

(10) Patent No.: US 12,303,364 B2
(45) Date of Patent: May 20, 2025

(54) ABSORBENT ARTICLES INCLUDING NON-ELASTICATED CUFFS

(71) Applicant: The Procter & Gamble Company, Cincinnati, OH (US)

(72) Inventors: Alexzandra Joan Spatholt, Cincinnati, OH (US); Edward Paul Carlin, Cincinnati, OH (US); Joshua Andrew Williams, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1200 days.

(21) Appl. No.: 16/693,743

(22) Filed: Nov. 25, 2019

(65) Prior Publication Data
US 2020/0170850 A1 Jun. 4, 2020

Related U.S. Application Data

(60) Provisional application No. 62/772,750, filed on Nov. 29, 2018.

(51) Int. Cl.
*A61F 13/475* (2006.01)
*A61F 13/15* (2006.01)
*A61F 13/47* (2006.01)

(52) U.S. Cl.
CPC .... *A61F 13/4758* (2013.01); *A61F 13/15203* (2013.01); *A61F 13/4704* (2013.01);
(Continued)

(58) Field of Classification Search
CPC ............ A61F 13/15203; A61F 13/4752; A61F 2013/15357; A61F 13/4758; A61F 2013/49042
See application file for complete search history.

(56) References Cited

U.S. PATENT DOCUMENTS 4,946,527 A * 8/1990 Battrell ............... A61F 13/5605
24/444
5,496,428 A 3/1996 Sageser
(Continued)

FOREIGN PATENT DOCUMENTS

CN 101610745 A 12/2009
CN 103582470 A 2/2014
(Continued)

OTHER PUBLICATIONS

CM5044M PCT Search Report and Written Opinion for PCT/US2019/062940 dated Mar. 12, 2020.

*Primary Examiner* — Michele Kidwell
(74) *Attorney, Agent, or Firm* — Sarah M. DeCristofaro; George H. Leal

(57) ABSTRACT

An absorbent article having a chassis formed of a topsheet and backsheet, and an absorbent core disposed between the topsheet and backsheet. First and second non-elasticated cuffs are provided on a body facing surface of the absorbent article on opposite sides of a longitudinal centerline. Each of the cuffs has a proximal end attached to the chassis and a distal end extending towards the centerline, wherein the width of the cuff measured between the proximal end and the distal end is at least 3 mm. Cuffs of the absorbent article may either incorporate a fold at the distal end to form cuffs with at least two layers or have a minimum cuff stiffness of at least 0.04 g*cm.

19 Claims, 7 Drawing Sheets

(52) U.S. Cl.
CPC .............. *A61F 2013/15357* (2013.01); *A61F 2013/15406* (2013.01); *A61F 2013/4708* (2013.01)

(56) References Cited

U.S. PATENT DOCUMENTS

| | | | |
|---|---|---|---|
| 6,117,121 A * | 9/2000 | Faulks | A61F 13/49017 604/385.29 |
| D539,905 S | 4/2007 | Amstadt | |
| D636,076 S | 4/2011 | Hood | |
| D641,867 S | 7/2011 | Hood | |
| 8,126,206 B2 | 2/2012 | Tsurumi | |
| D674,483 S | 1/2013 | Hood | |
| D705,927 S | 5/2014 | Hood | |
| D719,740 S | 12/2014 | Hood | |
| D737,433 S | 8/2015 | Hood | |
| D758,083 S | 6/2016 | Hood | |
| D759,233 S | 6/2016 | Gressle | |
| D766,428 S | 9/2016 | Gressle | |
| D815,275 S | 4/2018 | Hood et al. | |
| 2005/0004543 A1* | 1/2005 | Schroer | A61F 13/514 604/385.27 |
| 2008/0021426 A1* | 1/2008 | Nakagawa | A61F 13/5376 604/378 |
| 2011/0151196 A1* | 6/2011 | Schmidt | A47L 13/16 442/400 |
| 2016/0199234 A1* | 7/2016 | Long | A61F 13/49011 604/385.3 |
| 2016/0262950 A1* | 9/2016 | Liebe | A61F 13/47263 |
| 2016/0270973 A1* | 9/2016 | Surushe | A61F 13/55105 |
| 2017/0049636 A1* | 2/2017 | Hardie | A61F 13/475 |
| 2020/0093656 A1* | 3/2020 | Denti | A61F 13/47254 |

FOREIGN PATENT DOCUMENTS

| | | | | |
|---|---|---|---|---|
| CN | 107106372 A | | 8/2017 | |
| EP | 0 528 282 | * | 5/1993 | ............ A61F 13/15 |
| EP | 0631767 A1 | | 1/1995 | |
| JP | H06339497 A | | 12/1994 | |
| JP | 2001095844 A | | 4/2001 | |
| WO | WO0228335 A1 | | 4/2002 | |
| WO | WO0232362 A1 | | 4/2002 | |
| WO | DM/073651 | | 6/2010 | |
| WO | DM/084668 | | 9/2014 | |
| WO | DM/084644 | | 10/2014 | |

* cited by examiner

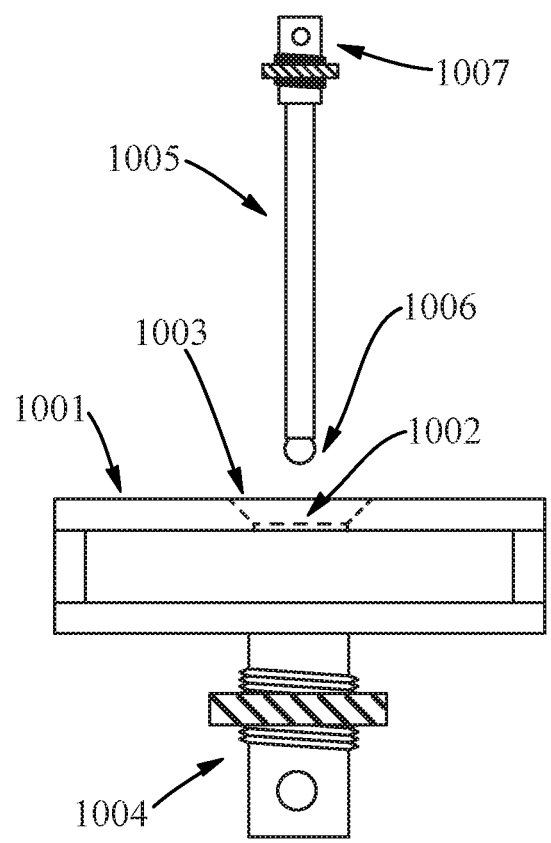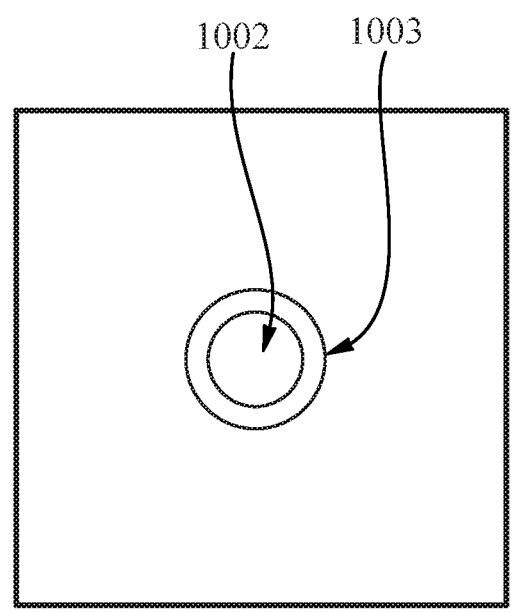
Figure 7A
Figure 7B

ABSORBENT ARTICLES INCLUDING NON-ELASTICATED CUFFS

FIELD OF THE INVENTION

The present invention relates to absorbent articles having first and second non-elasticated cuffs.

BACKGROUND OF THE INVENTION

Disposable absorbent articles having barrier cuffs are known and currently available on the market to help reduce the likelihood of leakage. In general, the barrier cuffs comprise a pre-strained elastic strand or plurality thereof which cause the barrier cuff to stand up relative to a top surface of the diaper or pad when in use.

Such barrier cuffs work exceptionally well with, for example, diapers that are intended to carry large volumes of exudates and where it is preferable to maintain a clear distance between the skin of the wearer and the soiled surface of the absorbent article. However, for cases where the volume of exudates is less and/or where the absorbent article is intended for daily use under regular clothing, these elasticated barrier cuffs may be uncomfortable and/or may result in a less discrete absorbent article. Inclusion of elasticated means also increases the cost of production of such articles.

On the contrary, particularly for adult incontinence pads intended to absorb urine, omitting the barrier cuffs completely can have a detrimental effect on the efficacy of the absorbent article. This is especially the case when, for example, there are periodic gushes of urine applied to the surface of the absorbent article. Even when the volume of the gush is small, it takes time for the urine to penetrate through the absorbent article and become fully absorbed—in this time, there is a risk of lateral leakage from the surface of the absorbent article.

Thus, there is a need for more comfortable barrier cuffs that still provide some protection against lateral leakage.

SUMMARY OF EXEMPLARY FORMS

The present invention is directed to an absorbent article having a longitudinal centerline, the absorbent article comprising: a) a chassis comprising a topsheet and backsheet; b) an absorbent core disposed between the topsheet and backsheet; c) first and second non-elasticated cuffs provided on a body facing surface of the absorbent article on opposite sides of the longitudinal centerline, each of said cuffs having a proximal end attached to the chassis and a distal end extending towards the longitudinal centerline, wherein the width of the cuff measured between the proximal end and the distal end is at least 3 mm and wherein each of said cuffs is formed of a single layer of material folded at the distal end to form a cuff with at least two layers.

Non-elasticated cuffs as described herein lie flush with the topsheet following manufacture of the absorbent article. Having a non-elasticated cuff of a certain width (i.e., the distance from proximal end to distal end of the cuff) that is folded at the distal end provides a cuff that, when the absorbent article is disturbed (for example during normal use), will stand-up relative to the topsheet, thus providing an effective barrier against lateral leakage of exudates from the surface of the absorbent article.

The present invention is further directed to an absorbent article having a longitudinal centerline, the absorbent article comprising: a) a chassis comprising a topsheet and a backsheet, b) an absorbent core disposed between the topsheet and the backsheet; c) first and second non-elasticated cuffs provided on a body facing surface of the absorbent article on opposite sides of the longitudinal centerline, each of said cuffs having a proximal end attached to the chassis and a distal end extending towards the longitudinal centerline, wherein the width of the cuff measured between the proximal end and the distal end is at least 3 mm and wherein each of said cuffs has a cuff stiffness of at least 0.04 g*cm.

Non-elasticated cuffs as described herein lie flush with the topsheet following manufacture of the absorbent article. Having a non-elasticated cuff of a certain width (i.e., the distance from proximal end to distal end of the cuff) and of a minimum stiffness provides a cuff that, when the absorbent article is disturbed (for example, during normal use), will stand-up relative to the topsheet, thus providing an effective barrier against lateral leakage of exudates from the surface of the absorbent article.

BRIEF DESCRIPTION OF THE DRAWINGS

The following detailed description of specific forms of the present invention can be best understood when read in conjunction with the drawings enclosed herewith.

FIGS. 7a and 7b are schematic illustrations of the test method and equipment for measuring Whole Pad Stiffness.

DETAILED DESCRIPTION

Figure 1:
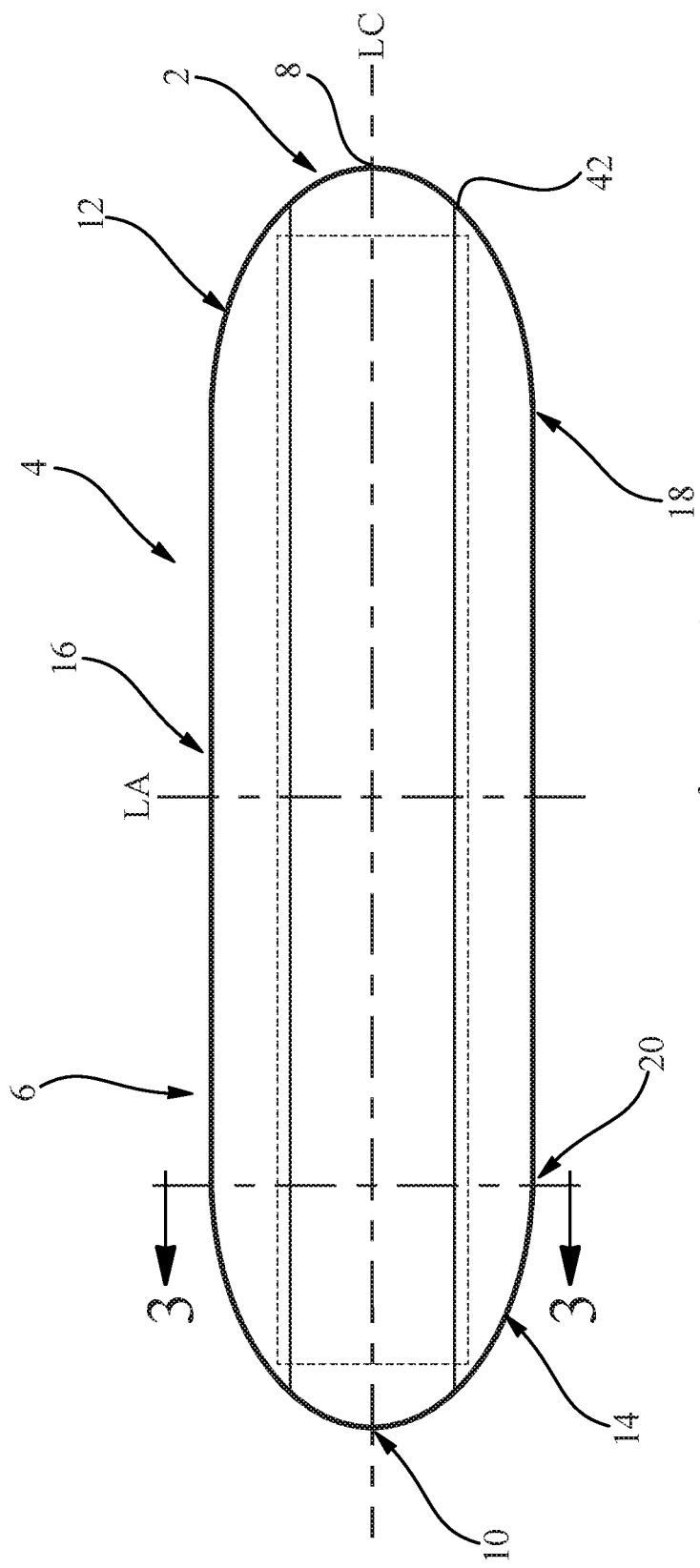
FIG. 1 is a schematic view from above of an absorbent article as described herein.

The present invention is generally directed to feminine hygiene articles, which are known to be absorbent articles worn externally by women, usually to absorb vaginal discharge and/or urine leakage. The term feminine hygiene articles includes such articles commonly referred to as pads, pantiliners, liners, sanitary napkins, sanitary towels, adult incontinence pads and interlabial devices. These articles are typically held in place adjacent the user's pubic region by the user's undergarment, and may be affixed thereto via adhesive or other joining means.

As used herein, the term "flush" means directly abutting or immediately adjacent to a recited portion of the article.

As used herein, the term "nonwoven web" refers to a web having a structure of individual fibers or threads which are interlaid, but not in a repeating pattern as in a woven or knitted fabric, which do not typically have randomly oriented fibers. The basis weight of nonwoven fabrics is usually expressed in grams per square meter (gsm). The basis weight of a nonwoven web/laminate is the combined basis weight of the constituent layers and any other added components. Fiber diameters are usually expressed in microns, fiber size can also be expressed in denier, which is a unit of weight per length of fiber.

As used herein, "spunbond" fibers" refer to small diameter fibers which are formed by extruding molten thermoplastic material as filaments from a plurality of fine, usually circular capillaries of a spinneret. Spunbond fibers are generally not tacky when they are deposited on a collecting surface. Spunbond fibers are generally continuous and have average diameters (from a sample of at least 10) larger than 7 microns, and more particularly, between about 8 and 40 microns.

As used herein "philic" and "phobic" have meanings as well established in the art with respect to the contact angle of a referenced liquid on the surface of a material. Thus, a material having a liquid contact angle of greater than about 75 degrees is considered phobic, and a material having a liquid contact angle of less than about 75 degrees is considered philic.

Absorbent articles described herein comprise a chassis with a topsheet and backsheet, an absorbent core disposed between the topsheet and backsheet and first and second non-elasticated cuffs provided on a body facing surface of the absorbent article on opposite sides of a longitudinal centerline. Each of the cuffs has a proximal end attached to the chassis and a distal end extending towards the longitudinal centerline, wherein the width of the cuff measured between the proximal end and the distal end is at least 3 mm. Cuffs of the absorbent article may either incorporate a fold at the distal end to form cuffs with at least two layers or have a minimum cuff stiffness of at least 0.04 g*cm. During manufacture, the first and second cuffs are positioned such that a distal end of each cuff, or a portion thereof, lies flush on a body facing surface of the absorbent article. During use, the distal ends of the cuffs, or a portion thereof, lift off the surface of the absorbent article such that the cuffs act as a barrier against lateral leakage of any exudates sitting on the surface of the absorbent article.

Elasticated cuffs are well known for providing security against side leakage of absorbent articles. The elastic creates tension in the cuffs, causing them to "stand-up" relative to the surface of the absorbent article to which they are attached. Such cuffs are particularly useful in adult incontinence absorbent articles that are expected to absorb a high volume of urine. The cuffs prevent leakage of the urine from the surface of the absorbent article, allowing time for the urine to penetrate into the article and be absorbed in the absorbent core. However, such elasticated cuffs are sometimes uncomfortable for users—particularly those who wish to use them on a daily basis. Furthermore, oftentimes absorbent articles used daily may not need to offer the same level of protection as provided by the elasticated cuffs. The present inventors have accordingly found a balance between the provision of some extra protection through use of non-elasticated cuffs that do not compromise on user comfort. Without being bound by theory, it is thought that having a minimum width enables the distal ends to lift off the topsheet and to provide a barrier to lateral leakage of liquid from the surface of the chassis—thus providing more time for the liquid to be absorbed by the absorbent article. Furthermore, increasing the stiffness (by providing a minimum stiffness or by introducing a fold at the distal end of the cuffs) provides a stronger cuff that is better able to withstand the force of liquids that may otherwise run off the topsheet.

The first and second cuffs may comprise two or more layers of material. Without being bound by theory, it is thought that providing multiple layers of material in the cuff increases the stiffness and strength of the cuffs. This results in buckling of the cuffs relative to the topsheet, thus causing the distal ends to stand-up relative to the topsheet. The increased strength enhances the ability of the cuffs to withstand forces from liquid pushing against the cuffs. Furthermore, use of multiple layers of material results in improved hydrophobicity that prevents fluid from passing through the cuffs. By providing cuffs having a distal end that extends some distance over the absorbent core, the elevation provided by the absorbent core relative to the surrounding chassis also assists with enabling the cuffs to "stand-up" relative to the topsheet.

Alternatively or additionally, the absorbent article may comprise panty fastening means on a garment facing surface of the backsheet. Where attachment means are provided, they are preferably located inboard of an attachment point of the first and second cuffs in a central section of the absorbent article. Without being bound by theory, it is thought that by positioning the panty fastening means inboard of the attachment point of the first and second cuffs, the distal end of each of the cuffs can bend/buckle separately from the garment to which it is attached as the article is moved. This is especially important in the central region of the pad, where the largest volume of exudate is likely to be received. This bending/buckling causes the distal ends of the cuffs to stand-up relative to the topsheet as the cuffs have more flexibility to move relative to the chassis and so are naturally inclined to stand up.

FIG. 1 shows an absorbent article 2 having a longitudinal centerline and a lateral centerline. The longitudinal centerline (LC) extends generally parallel to the longest dimension of the absorbent article. The lateral centerline (LA) extends generally perpendicular to the longitudinal centerline and lies in the same plane as the absorbent article in a flattened state on a flat surface. When referring to current conventional manufacture of absorbent articles, the machine direction (MD) may be generally parallel to the longitudinal centerline while the cross-machine direction (CD) may be generally parallel to the lateral centerline. The lateral centerline provides the boundary between the first half 4 and second half 6 of the absorbent article with the front end 8 being defined as that point towards the front of the article that extends furthest from the lateral centerline and the rear end 10 being defined at that point towards the rear of the article that extends furthest from the lateral centerline.

Figure 2A:
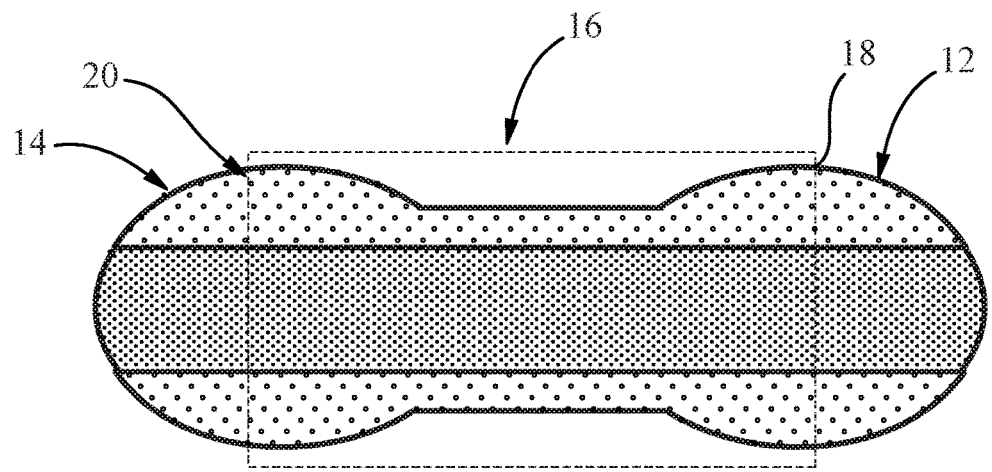
FIGS. 2a and 2b show schematically alternative forms of the absorbent article shown in FIG. 1.
Figure 2B:
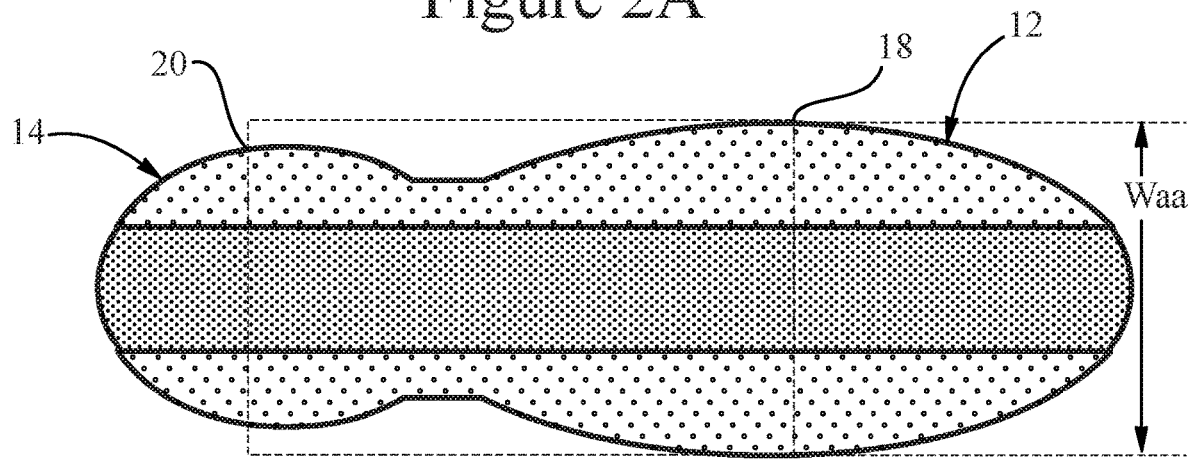

The absorbent article has three distinct sections—a front section 12, a rear section 14 and a central section 16. The central section 16 is usually that portion of the absorbent article 2 intended to receive the majority of exudates. In the embodiment shown in FIG. 1 that has a generally elongate oblong shape, the front section 12 is defined by the area of the article that tapers from the widest part 18 in the front of the article to the front end, likewise the rear section 14 is defined by that area of the article that tapers from a widest part 20 at the rear to the rear end. When considering a typical hourglass shape of absorbent article, as shown in FIG. 2a, or an offset hourglass shape, as shown in FIG. 2b, the front section may be defined as that area in the first half of the absorbent article extending from the widest part 18 to the front end of the absorbent article. The rear section 14 may be defined as that area in the second half of the absorbent article extending from the widest part 20 to the rear end of the absorbent article or vice versa. The central section 16 may be defined as the "waist" area between the widest part 18 in the first half and the widest part 20 in the second half.

Alternatively, in an absorbent article having a shape that has, for example, a wide rear and tapers towards the front (as is the case, particularly in some Night pads), the front section may be the first ⅓ of the pad extending from the front end towards the rear, the rear section may be the latter ⅓ of the pad extending from the rear end towards the front, and the central section may the ⅓ of the pad between the two.

In addition to those described above, it will be appreciated that the article may have a variety of different shapes, for example, an offset hourglass (where the front and rear ends are wider than the central section, and the absorbent article is symmetrical about the longitudinal centerline, but asymmetrical about the lateral centerline), bicycle seat shape (having a wide front or rear end that tapers towards the opposite end). Similar front, rear and central sections may be defined in all variations. The absorbent article may be symmetrical about the longitudinal centerline or asymmetric about the longitudinal centerline. Similarly, the absorbent article may be symmetric about the lateral centerline or asymmetric about the lateral centerline.

Figure 3:
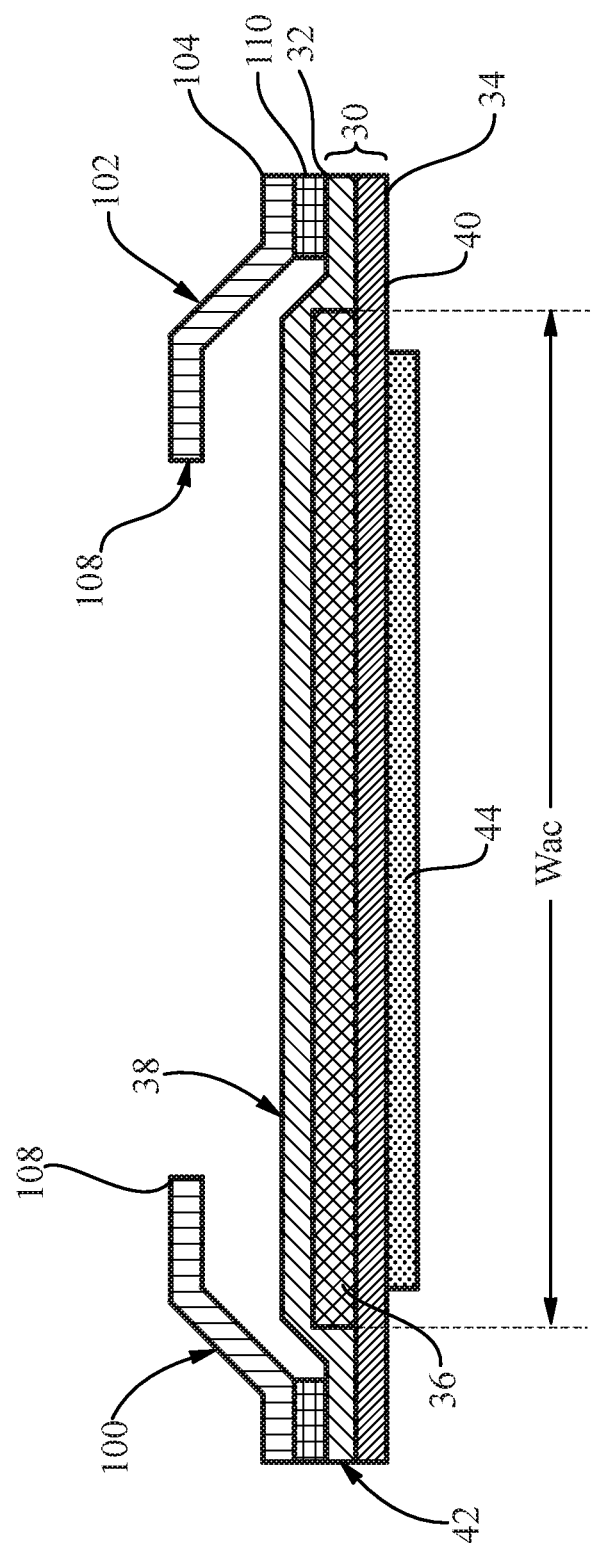
FIG. 3 shows a schematic lateral cross-section of the absorbent article shown in FIG. 1.

As shown in FIG. 3, the absorbent article has a chassis 30 comprising at least a topsheet 32 and backsheet 34 with an absorbent core 36 disposed therebetween, the topsheet 32 having a body facing surface 38 and the backsheet 34 having a garment facing surface 40. The topsheet and backsheet may be the same shape as shown in FIG. 3, such that the periphery 42 of the chassis 30 defines the overall shape of the absorbent article. Alternatively, the backsheet 34 may have a greater overall surface area than the topsheet 32 (not shown), thus minimizing the chance of wicking of fluid into the perimeter area of the article. In such embodiments, the overall footprint of the chassis is defined by the perimeter of the backsheet. Additional layers are contemplated between the topsheet and backsheet, for example secondary topsheets, acquisition layers, distribution layers and barrier layers. The absorbent article also typically comprises joining means 44 on the garment facing surface of the backsheet, to secure the absorbent article to a user's panties.

The topsheet 32 and backsheet 34 may be secured together by any known means, for example by crimping, adhering, thermally bonding, mechanically bonding or a combination of any known methods.

Absorbent articles such as those described herein may be folded to make the pad more consumer friendly and easier to transport and store. Fold lines about which the pad may be folded, tend to provide a natural bias for the distal ends to separate themselves from the topsheet. Thus, when a user unfolds a pre-folded pad, the distal ends may already "stand-up" along the pad lines. Thus, preferably, the absorbent article comprises a first fold line 50 and a second fold line 52 (shown in FIG. 4), dissecting the absorbent article into thirds. In an embodiment, the first and second fold lines may coincide with the boundaries between the front, central and rear sections. Thus, the distal ends are predisposed to separate from the topsheet particularly in the central section where the greatest amount of exudate is likely to be discharged onto the absorbent article.

Barrier Cuffs

As shown in FIG. 3, the absorbent article includes a first non-elasticated barrier cuff 100 provided on one side of the longitudinal centerline and a second non-elasticated barrier cuff 102 provided on the other side of the longitudinal centerline. "Non-elasticated" as used herein means the absence of elastic elements beyond the natural elasticity inherently found in the material itself. Thus, the barrier cuffs do not include any rubber thread, tape or other artefact that would increase the naturally occurring elastic properties of the cuff material.

The first and second barrier cuffs 100, 102 are provided at least in the central section 16 of the absorbent article 2, however, it will be appreciated that the first and second barrier cuffs may extend longitudinally from the front to the rear of the absorbent article. The first and second cuffs 100, 102 may be attached directly to the body facing surface 38 of the absorbent article, for example, the topsheet 32, or they may be attached at any other point on the absorbent article, for example, to the backsheet 34. The first and second barrier cuffs extend towards the longitudinal centerline of the absorbent article.

Post manufacture, the first and second barrier cuffs typically lie flush with the topsheet, wherein the distal ends extend upward only upon disturbance to the pad, for example, by folding for packing or during use by a consumer. The barrier cuffs serve to provide some extra protection to the absorbent article, particularly upon initial insult of the article with, for example, a sudden gush of urine. In such circumstances, it may take some time for the exudates to penetrate the absorbent article and reach the absorbent core. The first and second cuffs help limit sideways leakage from the top surface of the absorbent article.

The first and second cuffs have a proximal end 104 attached between the longitudinal centerline and a longitudinal edge of the chassis. Preferably, the proximal end of the respective barrier cuffs is coterminous with the longitudinal edge of the chassis, however, it will be appreciated that the proximal end of the barrier cuffs may also be located inboard of the longitudinal edge of the chassis. A distal end 108 of each of the first and second barrier cuffs extends towards the longitudinal centerline of the absorbent article. For the avoidance of doubt, at least in a central section of the absorbent article, the distal end 108 of each of the first and second cuffs is not attached to the topsheet or chassis. Thus, the distal end of the first and second cuffs in at least the central section of the chassis is free to lift up from topsheet, thus impeding lateral flow of exudates from the surface of the absorbent article.

Preferably, the width of the first and second barrier cuffs, i.e., that distance measured between the proximal end and the distal end in a direction substantially orthogonal to the longitudinal centerline is at least 3 mm, 4 mm, 5 mm, 6 mm, 7 mm or 8 mm. Without being bound by theory, it is thought that the cuffs need a minimum width such that the distal ends 108 separate from the topsheet and to "stand-up" relative to the topsheet. Where the width of the cuffs varies along the length of the respective cuffs, the width is measured at the lateral centerpoint of the absorbent article. This typically coincides with the minimum width of cuff in the central section of the absorbent article.

Preferably, the distal end of one or both of the first and second barrier cuffs extends over a portion of the absorbent core. Without being bound by theory, it is thought that the differential thickness and stiffness in the core area relative to the chassis increases the ease with which the cuffs may separate from the topsheet and "stand-up" relative to the topsheet. Thus, preferably, the first and second barrier cuffs extend over the absorbent core by at least 0.5 mm, 1 mm, 1.5 mm, 2 mm, 2.5 mm, 3 mm or 3.5 mm. Furthermore, to ensure that a sufficient surface area of the topsheet above the core is exposed to the user's body, the first and second barrier cuffs may extend over a total of between 1% and 70% of the width of the core $W_c$, as measured at the widest part of the core. At least 30% of the core should remain exposed to enable exudates to be absorbed.

Preferably, the extent to which the first and second barrier cuffs extends over the absorbent core does not exceed 40%, 35%, 30%, 25%, 20%, 15% or 10% of the overall width Wa of the absorbent article, as measured at its widest point. For example, for a pad having a maximum width of 100 mm, each cuff would be between 3 mm and 40 mm wide as measured along the widest point $W_{AA}$ of the absorbent article. There is a balance between providing cuffs that are wide enough to hold a sufficient amount of liquid, without being so wide that they become too heavy to lift off the topsheet and/or so wide that they cover the core making it harder for liquids to be absorbed.

The first and second cuffs may be attached to the chassis along the longitudinal edges of the absorbent article. Preferably, the first and second cuffs are in contact with and are attached to the topsheet, but embodiments where the cuffs may be attached between the topsheet and backsheet or to the backsheet may also be appreciated. Furthermore, in embodiments shown in FIGS. 5a and 5b, the cuffs may be formed as an extension of either the topsheet or the backsheet.

Figure 4:
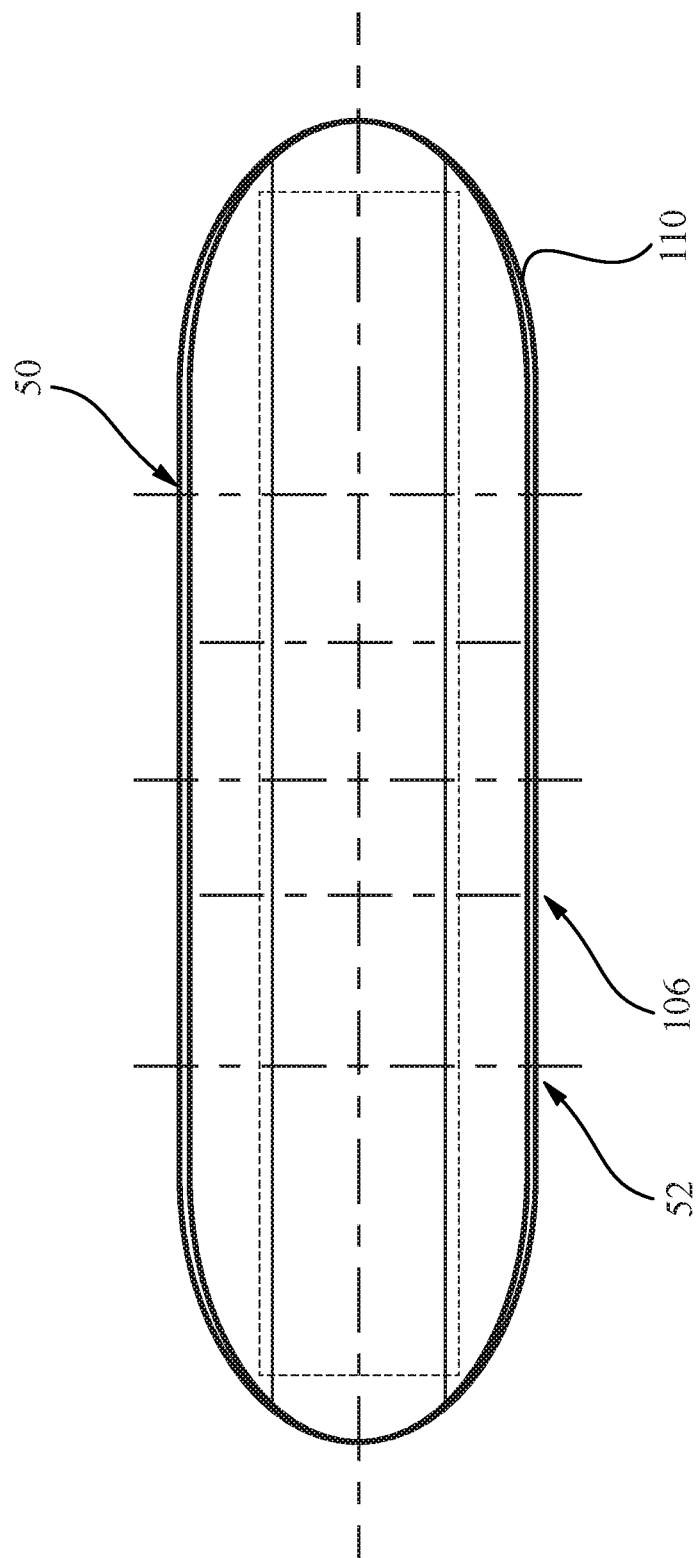
FIG. 4 shows the schematic of FIG. 1 with additional details highlighted.

An attachment strip 110, shown in FIGS. 3 and 4, is provided at the proximal end of each cuff, typically in line with the longitudinal edges of the chassis although, as mentioned above, the cuffs may be attached inboard of the edges of the chassis. The cuffs may be crimped together with the chassis and/or adhered in some other known way, for example, with adhesive. Preferably, the cuffs are both crimped and adhered to the chassis. By crimping and adhering the cuffs to the chassis, it is possible to better control the behavior of the cuffs, both during manufacture and use.

Preferably, the attachment strip has a width of between 1 mm and 20 mm, 2 mm and 17 mm, 3 mm and 15 mm, 4 mm and 12 mm, 5 mm and 10 mm, 6 mm and 9 mm, extending from the proximal edge of the cuffs. In the front and rear sections of the absorbent article, and particularly at the front and rear ends of the chassis, the cuffs may be crimped, adhered or otherwise attached to the topsheet from some or all of the area from the proximal end to the distal end. Securing the distal ends of the cuffs in the front and rear sections creates extra tension in the cuffs that further enables them to stand-up in the central section relative to the topsheet and provides better control during manufacture.

Figure 5A:
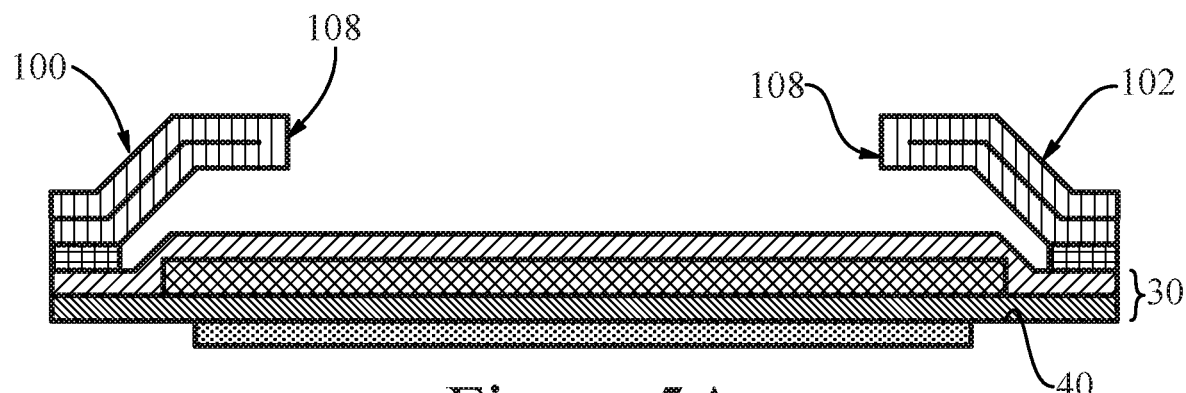
FIGS. 5a, 5b and 5c show schematically alternative forms of cuff as provided on an absorbent article as described herein.
Figure 5B:
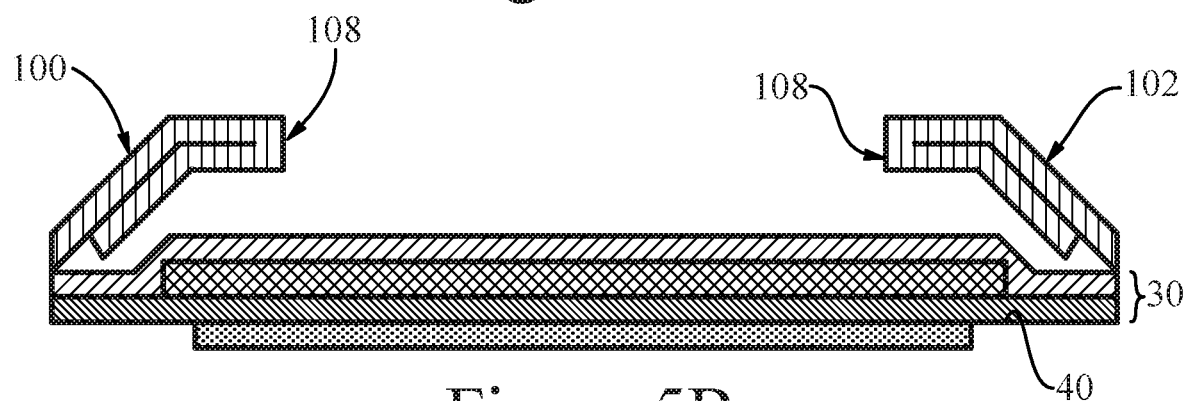
Figure 5C:
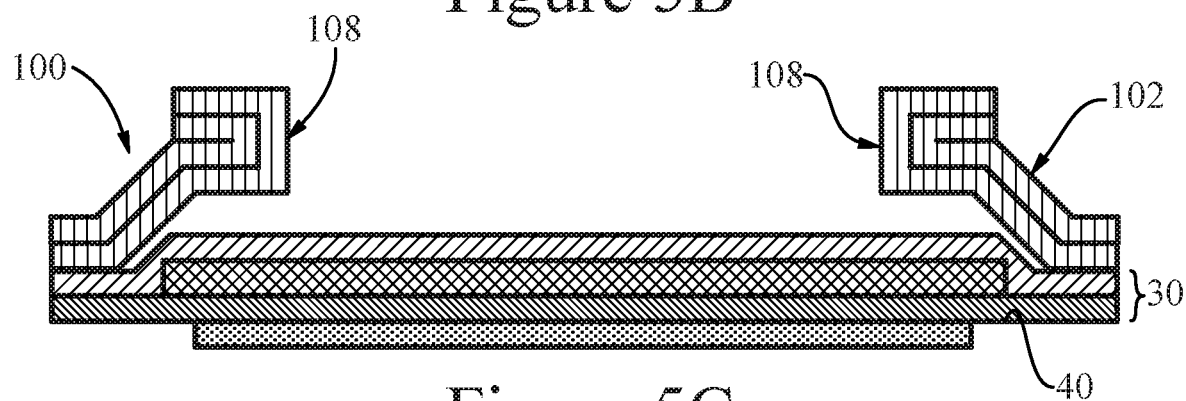

In embodiments, the first and second barrier cuffs may be formed of more than one layer of material, as shown in FIGS. 5a, 5b and 5c. Providing more than one layer effectively increases the overall stiffness and strength of the cuff, thus enabling it to more easily separate from the topsheet and therefore stand-up relative to the topsheet, thus providing better protection while in use. The multiple layers also provide better protection against liquid passing through the cuffs and more strength when fluids enter under the cuff.

Where the first and/or second cuffs include multiple layers, the cuffs may be formed of multiple strips of material attached together, either at the attachment strip, or at a distal end. Alternatively, the cuffs may comprise one or more folds formed of a single piece of material to form cuffs with multiple layers. Where the cuff is folded, one, all or select layers of the folded cuff may be attached directly to the chassis, as shown in FIG. 5a. In an alternative embodiment shown in FIG. 5b, the first and second cuffs comprise a single piece of material folded at a distal end of the cuff to form a dual layer cuff, where only one end of the material is attached to the chassis and where the other end of the material is attached to the cuff itself. FIG. 5c shows yet another alternative where two layers of material make up the cuff and are folded back on one another, then a portion of the combined material is folded back at the distal end.

Providing a fold in the material biases the cuff to more naturally separate itself from the topsheet during use. Without being bound by theory, it is thought that the fold introduces some natural resilient tension into the cuff, such that the cuff has a natural tendency to return to an un-folded state, which causes the cuffs to "stand-up" relative to the topsheet.

Using multiple layers increases the collective stiffness of the cuff relative to using a single layer of material with a higher basis weight. Thus, it is possible to use thinner material, for example, the topsheet material, and to achieve the benefits of a stiffer material that results in separation of the cuffs from the topsheet and enables the cuffs to stand up relative to the topsheet.

The cuffs may be formed of the same material as the topsheet. Using the same material as the topsheet reduces manufacturing costs, for example by enabling bulk order of material and by reducing complexity at the manufacturing line by reducing the number of unwinds (and corresponding space) needed for introducing extra materials. Where the cuffs are formed of the same material as the topsheet, they may be treated to make them phobic.

The cuffs (including single layer, multiple layer and folded cuffs) have a cuff stiffness of at least 0.04 g*cm, 0.05 g*cm, 0.1 g*cm, 0.25 g*cm, 0.5 g*cm or 0.8 g*cm, as measured by the cuff stiffness test described herein. This test measures a sample of the cuff removed from a finished absorbent article. Where the cuff incorporates a fold, the sample includes the fold such that the test method measures the folded stiffness (as opposed to raw material stiffness). Likewise, where the cuff is formed of multiple layers, the cuff stiffness test method measures the stiffness of the combined layers.

The cuffs may have a thickness of between 0.01 mm and 1.5 mm, 0.04 mm and 1.25 mm, 0.1 mm and 1.0 mm, 0.25 mm and 0.75 mm. As above, the measure of thickness is taken of the cuff on the finished article and includes single material, multi-layer material and/or folded cuffs. The barrier cuffs may have a basis weight of between 5 gsm to 100 gsm, 15 gsm to 85 gsm, 30 gsm to 70 gsm, 40 gsm to 60 gsm.

The first and second cuffs may extend through a central portion of the absorbent article, or they may extend in a longitudinal direction from the front to the rear of the absorbent article. Alternatively, more than two cuffs may be provided—for example, first and second cuffs may be provided in the central section, with one or more separate cuffs provided in the central section and/or one or both of the front and rear sections. Alternatively, the first and second cuffs may extend from the central section to one or both of the front and rear sections of the absorbent article, with one or more additional cuffs provided at one or both of the respective ends. In an embodiment, the one or more cuffs provided at one or both of the ends of the absorbent article may have distal ends extending substantially in parallel to the longitudinal centerline or they may be oriented at an angle relative to the longitudinal centerline.

The first and second cuffs may be made from hydrophilic or hydrophic materials, topsheet or backsheet, Spunbond meltblown spunbond (SMS) or other nonwovens with melt blown layers. The cuffs may also be made of synthetic or natural fibers such as polyethylene, polypropylene, polyester materials, polyamides (e.g., nylon), cotton, silk or pulp which has been spunbonded, carded, melt blown, or a combination of similar known methods. The first and second cuffs may be made from the same material as one of the topsheet or the backsheet, thus reducing raw material costs. Preferably, the cuffs are formed of SMS.

Primary Topsheet

As previously mentioned, the primary topsheet (also referred to herein as "topsheet") of the chassis provides a body-facing surface of the absorbent article and may be joined to the backsheet by attachment methods known in the art. The topsheet and the backsheet may be joined directly to each other around the periphery of the absorbent article and (or may be indirectly joined together through the absorbent core or additional optional layers within the chassis (for example, a secondary topsheet which spans the entire area of the chassis).

The absorbent article may comprise any known or otherwise effective primary topsheet, such as one which is compliant, soft feeling, and non-irritating to the wearer's skin. Suitable primary topsheet materials include a liquid pervious material that is oriented towards and contacts the body of the wearer permitting bodily discharges to rapidly penetrate through it without allowing fluid to flow back through the topsheet to the skin of the wearer. The primary topsheet, while being capable of allowing rapid transfer of fluid through it, also provides for the transfer or migration of the lotion composition onto an external or internal portion of a wearer's skin. A suitable topsheet can be made of various materials such as woven and nonwoven materials; aperture film materials including aperture formed thermoplastic films, aperture plastic films and fiber-entangled aperture films; hydro-formed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135, 4,324,246; 4,342,314; 4,463,045; 5,006,394; 4,609,518; and 4,629,643.

Nonlimiting examples of woven and nonwoven materials suitable for use as the topsheet include fibrous materials made from natural fibers, modified natural fibers, synthetic fibers, or combinations thereof. Some suitable examples are described in U.S. Pat. Nos. 4,950,264, 4,988,344, 3,978,185, 7,785,690, 7,838,099, 5,792,404, and 5,665,452.

In some forms, the topsheet may comprise tufts as described in U.S. Pat. Nos. 8,728,049, 7,553,532, 7,1272, 801, 8,440,286, 7,648,752, and 7,410,683. The primary topsheet may have a pattern of discrete hair-like fibrils as described in U.S. Pat. No. 7,655,176 or 7,402,723. Additional examples of suitable topsheets include those described in U.S. Pat. Nos. 8,614,365, 8,704,036, and 6,025,535.

Another suitable primary topsheet or a primary topsheet combined with a secondary topsheet may be formed from a three-dimensional substrate as detailed in US. Patent Application No. 2017/0258647.

The primary topsheet may have one or more layers, as described in U.S. Patent Application Nos. 2016/0167334, 2016/0166443, 2017/0258651. The topsheet may be aperture as disclosed in U.S. Pat. No. 5,628,097.

Secondary Topsheet

As noted previously, the absorbent article may comprise additional layers, one of which includes a secondary topsheet. As mentioned previously, the secondary topsheet may be separate and apart from the absorbent system. The secondary topsheet is preferably disposed beneath the primary topsheet and on the body-facing surface of the core and may function to help move liquid from the topsheet to the core, typically acquiring and distributing fluid. The secondary topsheet may have a basis weight of between 40 gsm to 150 gsm.

Some exemplary secondary topsheets are described in U.S. Patent Application Nos. 2015/0351976 and 2014/034523 and U.S. application Ser. No. 15/729,704.

Backsheet

The backsheet of the chassis may provide a garment-facing surface of the absorbent system and may be joined to the topsheet, absorbent core and/or other layers as appropriate by attachment methods known in the art. For example, the backsheet may be secured to the garment facing surface of the absorbent core by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated where the absorbent system is not joined to eth backsheet, the topsheet or both.

The backsheet may be impervious, or substantially impervious, to liquids (e.g., urine) and may be manufactured from a thin plastic film, although other flexible impervious materials may also be used. As used herein, the term "flexible" refers to materials which are compliant and will readily conform to the general shape and contours of the human body. The backsheet may prevent, or at least inhibit, the exudates absorbed and contained in the absorbent system from wetting articles of clothing which contact the absorbent article, such as undergarments. However, in some instances, the backsheet may be breathable and a secondary barrier layer with a smaller surface area than the backsheet may be provided between the core and the backshseet.

The backsheet may comprise a polymeric film such as thermoplastic films of polyethylene or polypropylene. A suitable material for the backsheet is a thermoplastic film having a thickness of from about 0.012 mm to about 0.050 mm, for example. Any suitable backsheet known in the art may be utilized with the present invention.

Some suitable examples of backsheets are described in U.S. Pat. Nos. 5,885,265, 4,342,314, and 4,463,045. Suitable single layer breathable backsheets for use herein include those described for example in GB 2184389, GB2184390, U.S. Pat. No. 3,989,867, Wo 97/24097 and U.S. Pat. Nos. 6,623,464, 6,664,439 and 6,436,508.

The backsheet may have two layers, a first layer comprising a gas permeable aperture formed film layer and a second layer comprising a breathable microporous film layer as described in U.S. Pat. No. 6,462,251. Suitable dual or multi-layer breathable backsheets for use herein include those exemplified in U.S. Pat. Nos. 3,881,489, 4,341,489, 4,341,216, 4,713,068, 4,818,600, EP 203821, EP 710471, EP 710472 and EP 793952.

Absorbent Core

The absorbent system/core of the present invention may comprise any suitable shape. The absorbent system is typically the stiffest portion of the absorbent article. Thus, shapes which are useful for the articles of the present disclosure may comprise a reduced width central region, as this is typically the narrowest area during use. For example, the absorbent system may comprise a dogbane shape where it is narrower in the central region than in the end regions. Alternatively, the absorbent system may comprise a tapered shape having a wider portion in one end region of the pad which tapers to a narrower central and end region in the other end of the pad. Alternatively, the absorbent core may have a symmetrical or asymmetrical oval or diamond shape, having a wider portion in the central region with narrower portions at one or both ends. The absorbent system may comprise varying stiffness in the MD and CD.

The absorbent system comprises at least an absorbent core but may also comprise a first absorbent core and second absorbent core. The absorbent core (or first and second absorbent cores) may comprise a single layer or multiple layers positioned above one another, having the same overall surface shape and size or having different surface shapes and sizes. Alternatively, where the absorbent core is made of different sections of absorbent core, they may also be located within the same plane, for example, with a first absorbent core located in the center and the second (or more) absorbent core(s) located to the sides or at the front and/or rear of the first absorbent core. In general, the absorbent system should be compressible, conformable, non-irritating to the wearer's skin, and capable of absorbing and retaining liquids such as urine and other certain body exudates including menses.

The configuration and construction of the absorbent system may vary (e.g., the absorbent system may have varying caliper zones, a hydrophilic gradient, a superabsorbent gradient, or lower average density and lower average basis weight acquisition zones). Further, the size and absorbent capacity of the absorbent system may be varied to accommodate a variety of wearers or forms of absorbent article. However, the total absorbent capacity of the absorbent system should be compatible with the design loading and the intended use of the absorbent article.

Absorbent cores comprising relatively high amounts of super absorbent polymer with various core designs are disclosed in U.S. Pat. No. 5,599,335, EP 1,447,066, WO 95/11652, US Patent No. 2008/0312622 and WO 2012/052172.

The absorbent cores described above may comprise superabsorbent polymers (SAP) or absorbent gelling materials (AGM), often in the form of particles or fibers. In general, such SAP materials have been used for their fluid absorbing properties. Such materials form hydrogels on contact with liquid (e.g., with urine, blood, and the like).

The size of the fluid absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Fluid absorbent gelling material particles preferably have a particle size of from about 30 microns to about 2 mm for substantially all of the particles. "Particle Size" as used herein means the weighted average of the smallest dimension of the individual particles. The absorbent core may comprise SAP and less than 15%, less than 10%, less than 5% less than 3% or less than 1% of airfelt or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers ("SAP"), or any equivalent material or combinations of materials.

The configuration and construction of the absorbent core may vary (e.g., the absorbent system may have varying caliper zones, a hydrophilic gradient, a superabsorbent gradient, or lower average density and lower average basis weight acquisition zones; or may comprise one or more layers or structures, for example different patterns of SAP of zones not containing SAP). Further, the size and absorbent capacity of the absorbent core may also be varied to accommodate a variety of wearers. However, the total absorbent capacity of the absorbent core should be compatible with the design loading and the intended use of the feminine pad.

In certain forms of the present invention, the absorbent core can be relatively thin, such as, for example, less than about 10 mm, or less than about 5 mm in thickness, or less than about 3 mm, or less than 1 mm in thickness. Thickness can be measured by any means known in the art for doing so while the core is under a uniform pressure of 0.25 psi.

In some forms, the absorbent core may comprise a plurality of multi-functional layers. For example, the absorbent core may comprise a core wrap (i.e., the layers enclosing the absorbent material of the absorbent structure). The core wrap may be formed by two nonwoven materials, substrates, laminates, films, or other materials. In a form, the core wrap may only comprise a single material, substrate, laminate, or other material wrapped at least partially around itself. Additional layers contemplated are acquisition and distribution layers which are well known in the art.

The absorbent core may comprise one or more adhesives, for example, to help immobilize the SAP or other absorbent materials within the core and/or to ensure integrity of the core wrap, in particular when the core wrap is made of two or more substrates. The core wrap may extend to a larger area than required for containing the absorbent material(s) within.

The absorbent material may comprise one or more layers present within the core wrap with channels having no, or little (e.g., 0.1% to 10%) absorbent material positioned therein. In other forms, the absorbent material may be formed as individual pockets or stripes within eth core wrap. In the first case, the absorbent material may be, for example, obtained by the application of a continuous layer (s) of absorbent material, with the exception of the absorbent material free, or substantially free, channels. The continuous layer (s) of absorbent material, in particular of SAP, may also be obtained by combining two absorbent layers having discontinuous absorbent material application patterns, wherein the resulting layer is substantially continuously distributed across the absorbent particulate polymer material area.

The absorbent structure may be a heterogenous mass comprising enrobable elements and/or one or more portions of foam pieces, such as open-celled foam. The enrobeable elements may be a web such as, for example, nonwoven, a fibrous structure, an airlaid web, a wet laid web, a high loft nonwoven, a needle-punched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof. The foam may be a high internal phase emulsion (HIPE) foam.

Test Methods

Stand Up Cuff Height

The maximum height of a cuff attached to an absorbent article is measured using optical profilometry to obtain the areal surface topology of the body facing side of the article that is mounted to the inside of a curved backing plate. All sample preparation and testing are performed in a laboratory maintained at 23° C.±2 C° and 50%±2% relative humidity, and test samples are equilibrated in this environment for at least 2 hours prior to testing.

Three-dimensional (3D) surface topography images of each test sample are recorded using an optical 3D surface topography measurement system. A suitable optical 3D surface topography measurement system is the MikroCAD Premium instrument commercially available from LMI Technologies Inc., Vancouver, Canada, or equivalent. The system includes the following main components: a) a Digital Light Processing (DLP) projector with direct digital controlled micro-mirrors; b) a CCD camera with at least a 1600×1200 pixel resolution; c) projection optics adapted to a measuring area of at least 140 mm×105 mm; d) recording optics adapted to a measuring area of 140 mm×105 mm; e) a table tripod based on a small hard stone plate; f) a blue LED light source; g) a measuring, control, and evaluation computer running surface texture analysis software (a suitable software is MikroCAD software with MountainsMap technology, or equivalent); and h) calibration plates for lateral (XY) and vertical (Z) calibration available from the vendor.

The optical 3D surface topography measurement system measures the surface height of a sample using the digital micro-mirror pattern fringe projection technique. The result of the measurement is a 3D image of surface height (defined as the Z axis) versus displacement in the horizontal (XY) plane. This 3D data set can also be thought of as an image in which every pixel in the image has an associated XY displacement, and the value of the pixel is the recorded Z-axis height value. The system has a field of view of 140×105 mm with an XY pixel resolution of approximately 85 microns, and a height resolution of 0.5 microns, with a total possible height range of 32 mm.

The instrument is calibrated according to manufacturer's specifications using the calibration plates for lateral (XY plane) and vertical (Z axis) available from the vendor.

Prior to imaging, test samples are mounted to a curved backing plate made of Plexiglass (or equivalent) with an inner radius of curvature equal to 149 mm. The length and width of the curved backing plate are equivalent to the length and width of the test sample such that it is fully supported when mounted, without blocking the projected light from the instrument.

To prepare the test sample, unfold the absorbent article if necessary and remove any wrapper present. Using minimal handling, mark a crosshair symbol at the midpoint of the article on the body facing side of the test sample. The midpoint is the intersection of the longitudinal and lateral midlines of the absorbent article. Additionally, mark lines on the body facing side of the test sample that are parallel to the lateral axis of the test sample and denote longitudinal quartiles such that each marked section represents about 25% of the overall length of the article.

Mount the test sample to the inside concave surface of the curved backing plate as follows. Gently place a small piece of double sided tape (such as 3M 665 or equivalent, from any convenient source) onto the garment facing side of the test sample at the midpoint and at each longitudinal end. If the test sample contains adhesive on the garment facing side, this can be used as an alternative to the double sided tape. Position the longitudinal axis of the test sample parallel to the curvature of the backing plate and align the midpoint of the test sample with the midpoint of the curved backing plate. Once aligned, gently press the center of the test sample against the curved plate using minimal but sufficient force to attach it. Without touching the cuffs, carefully flatten the test sample against the plate, and gently press at each longitudinal end using minimal but sufficient force to attach them to the plate to complete the mounting process. The test sample should now be conformed to the curvature of the plate.

The mounted test sample is placed onto the MikroCAD table beneath the camera. Orient the test sample such that the longitudinal axis of the test sample is parallel to the long axis (X axis) of the instrument's field of view. A 3D surface topology image of the middle half of the test sample ($2^{nd}$ and $3^{rd}$ quartiles), including both cuffs, is collected by following the instrument manufacturer's recommended measurement procedures. This step will include focusing the measurement system and performing a brightness adjustment. No pre-filtering options are used. The collected height image file is saved to the evaluation computer running the surface texture analysis software. In like fashion, images are collected for five substantially similar absorbent article test samples for each test product evaluated.

If the field of view of the 3D surface topography measurement system is inadequate to capture the entire area containing the middle half of the test sample and both cuffs, multiple scans over the surface overlapping by at least 20 area % are acquired (maintaining the XY resolution) and digitally stitched together to generate a single 3D surface topography image for subsequent analysis.

The 3D surface topography image is opened in the surface texture analysis software. The following filtering procedure is then performed on each image: 1) removal of invalid points; 2) a 7×7 pixel median filter to remove noise; and 3) a morphological closing operation (a dilation followed by an erosion) using a 9 pixel radius circular structuring element to smooth the surface and close holes inconsistent with the apparent surface of the article, due to a low basis weight material for example.

The following analysis is performed on the filtered 3D topography image. The maximum height (Z axis) of the first cuff is determined along its middle half ($2^{nd}$ and $3^{rd}$ quartiles) at each position along the X axis and recorded to the nearest 0.1 mm. Corresponding height (Z axis) values are determined at each position along the topsheet of the absorbent article immediately inboard and adjacent to the first cuff and recorded to the nearest 0.1 mm. The difference between each maximum first cuff height value and its corresponding topsheet height value is calculated and recorded as a Cuff Height value to the nearest 0.1 mm. In like fashion, this procedure is repeated for the second cuff on the test sample, and the difference between each maximum second cuff height value and its corresponding topsheet height value is calculated and recorded as a Cuff Height value to the nearest 0.1 mm. Calculate the average of all Cuff Heights measured on this test sample and record to the nearest 0.1 mm. Determine the length of the middle half ($2^{nd}$ and $3^{rd}$ quartiles) of the test sample along which the cuff heights were measured, and record as Cuff Length to the nearest 0.1 mm. Now multiply the average Cuff Height (in mm) by the Cuff Length (in mm) and record as Cuff Area to the nearest square millimeter. In like fashion, analyze the 3D topography images for the remaining four replicate test samples.

Report Stand Up Cuff Height as the arithmetic mean of all Cuff Height values measured across all five replicate test samples to the nearest 0.1 mm. Report the Average Cuff Area as the arithmetic mean of all Cuff Area values measured across all five replicate test samples to the nearest square millimeter.

Curved CD Run-Off

The curved CD Run-Off test measures the amount of liquid that runs over the lateral edge of an absorbent article after a specified amount of test liquid is applied. An absorbent article is mounted on a curved plate that is arranged at a 30° angle, with the article's longitudinal axis perpendicular to the incline angle and parallel to the curvature of the plate. A single gush of liquid is dosed at the midpoint of the article. Liquid that is not captured by the absorbent article runs off the lateral edge. The run-off liquid is collected and its mass is recorded. All measurements are performed in a laboratory maintained at 23° C.±2 C° and 50%±2% relative humidity, and samples are conditioned in this environment for at least 2 hours prior to testing.

Figure 6:
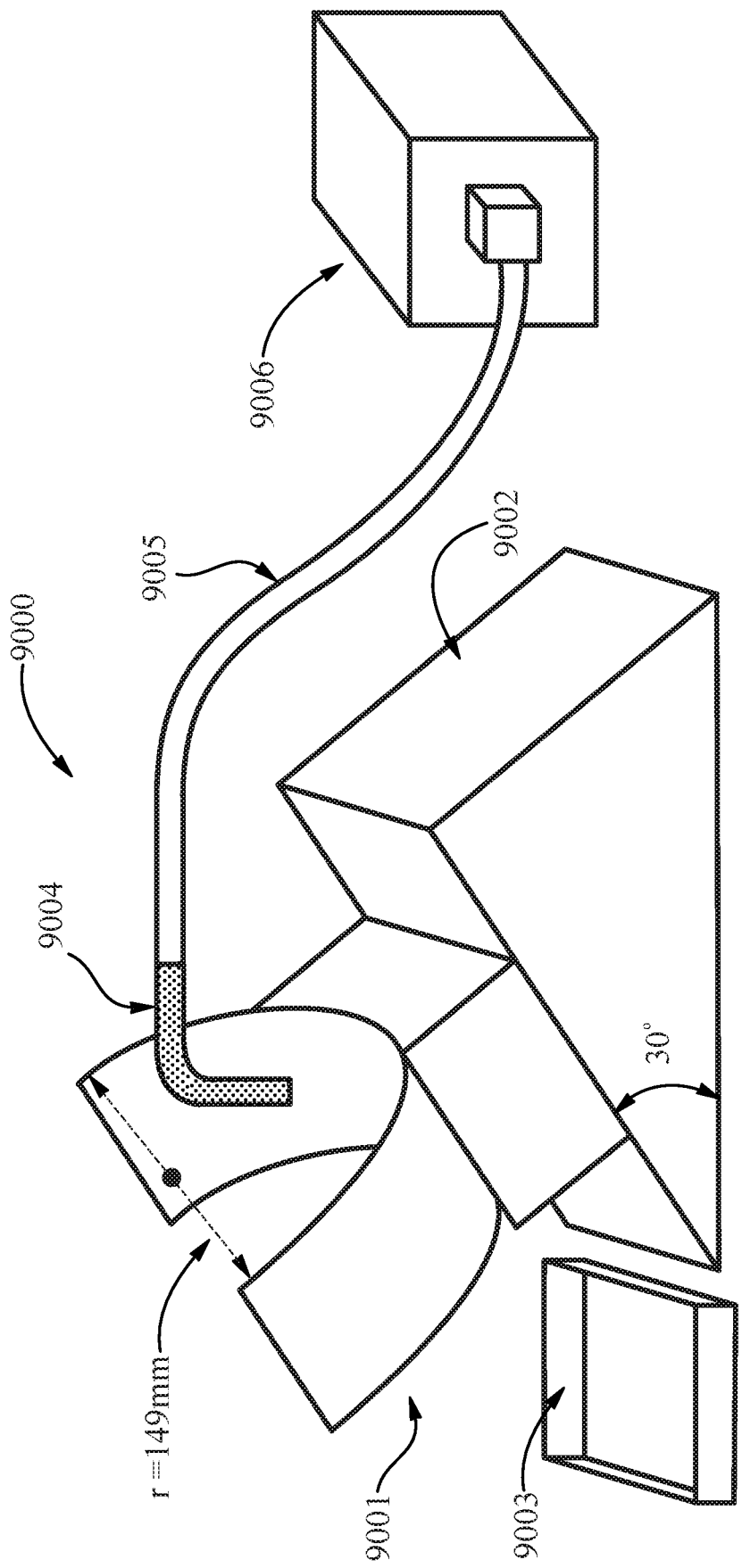
FIG. 6 is a schematic illustration of the test method and equipment used to measure curved CD Run-off.

The curved CD Run-Off equipment is depicted in FIG. 6. The curved run-off plate 9001 consists of Plexiglass (or equivalent) that is about 3 mm thick. It has a radius of curvature equal to 149 mm with a width and length adequate to hold the sample being tested. The curved run-off plate 9001 is mounted to an incline table 9002 whose angle is set at 300. The height of the lowest point of the curved run-off plate 9001 is at least 30 mm above the lab bench so the collection tray 9003 can easily be positioned on the bench beneath it. The collection tray 9003 consists of Plexiglass (or equivalent) and is of a suitable size (e.g. 100 mm wide×305 mm long×25 mm tall) to collect the run-off liquid. Mounted vertically above the curved run-off plate 9001 is a liquid dosing tube 9004 connected to a liquid pump 9006 via Tygon tubing 9005. The dosing tube 9004 is stainless steel (or equivalent) and has an inner diameter of 4.0 mm. The liquid pump 9006 (Ismatec MCP-Z gear pump, available from Cole Palmer, Vernon Hills, IL, or equivalent) is capable of delivering a flow of 10-60 mL at a rate of 10 mL/s.

The test solution is 0.9% w/v saline. To prepare 1 L of test solution, add 9.0 g±0.05 g of reagent grade NaCl to a 1 L volumetric flask then diluting to volume with de-ionized water. The pump 9006 is primed and then calibrated to deliver each size dependent volume and flow rate as defined in Table I below. Volume and flow rate must be within 2% of target.

TABLE I

Size Dependent Volumes and Flow Rates for Run-Off Testing

| Pad Length (mm) | Volume (mL) | Rate (ml/sec) |
|---|---|---|
| <275 | 10.0 | 10 |
| 276-320 | 15.0 | 10 |
| 321-350 | 20.0 | 10 |
| 351-375 | 25.0 | 10 |
| >375 | 30.0 | 10 |

To prepare a test sample, unfold the absorbent article, if necessary, and using minimal handling, mark the midpoint of the article on the body facing side of the test sample. The midpoint is the intersection of the longitudinal and lateral midlines of the absorbent article. Remove any wrapper that is present and record the mass of the test sample as Dry Pad Mass to the nearest 0.01 grams.

Mount the garment facing side of the test sample to the surface of the curved run-off plate 9001 using the adhesive on the backsheet of the test sample, if present, or use double sided tape (such as 3M 664, or equivalent from any convenient source). Orient the test sample such that its longitudinal axis runs perpendicular to the incline angle and its midpoint is aligned with the midpoint of the curved run-off plate 9001. Place 2 folded paper towels into the collection tray 9003 and record the mass of the tray+paper towels as Initial Tray Mass to the nearest 0.01 grams. Place the collection tray 9003 containing the paper towels under the front lateral edge of the curved run-off plate 9001 so that it can capture any liquid that runs off the test sample. Center the dosing tube 9004 25.0 mm above the midpoint of the body facing surface of the test sample and start the pump 9006 to deliver the prescribed dose of 0.9% w/v saline solution. After the dose has been applied, use the paper towels from the collection tray 9003 as needed to collect any drops of test liquid that remain on the incline table 9002. Record the mass of the tray+paper towels as Final Tray Mass to the nearest 0.01 grams. Record the mass of the test sample as Wet Pad Mass to the nearest 0.01 grams. Calculate the amount of liquid retained by the test sample as the difference between the Wet Pad Mass and Dry Pad Mass and record as Fluid in Pad to the nearest 0.01 grams. Calculate the amount of liquid that ran off the test sample as the difference between the Final Tray Mass and the Initial Tray Mass and record as Fluid in Tray to the nearest 0.01 grams. Finally, calculate % CD Run-Off as [Fluid in Tray/(Fluid in Pad+Fluid in Tray)]*100 and report to the nearest 1%.

In like fashion, repeat for a total of ten replicate test samples where five of these replicates test the cuff on one lateral side of the absorbent article and the other five replicates test the cuff on the opposite lateral side. Calculate and report the arithmetic mean for % CD Run-Off to the nearest 1%.

Cuff Stiffness

The stiffness of a test specimen is measured using a Taber Stiffness Tester (model 150-B, Taber Industries, North Tonawanda, N.Y.), equipped with a high sensitivity attachment (SR, Sensitivity Range) and a 10 unit compensator (both available from Taber Industries). For this setup, a 15 degree deflection to the right is used to measure each test specimen in the machine direction. The system is calibrated and operated per the manufacturer's instructions. All measurements are performed in a laboratory maintained at 23° C.±2 C° and 50%±2% relative humidity and test specimens are conditioned in this environment for at least 2 hours prior to testing.

Obtain a test specimen by removing it from an absorbent article, if necessary. When excising the test specimen from an absorbent article, use care to not impart any contamination or distortion to the region containing the test specimen during the process. The test specimen is obtained from an area free of folds or wrinkles, near the longitudinal midpoint of the absorbent article. The presentation of the test specimen in the absorbent article must be represented during this test (e.g. if folded to give multiple layers, the stiffness of all layers including the fold is measured). An ideal test specimen has a 3.81 cm width (parallel to the lateral axis of the absorbent article) and a 3.81 cm length (parallel to the longitudinal axis of the absorbent article). To accommodate testing of a narrow region, a smaller test specimen can be used, however it must have a length of 3.81 cm, be rectangular in shape (e.g. no curved edges) with a width as large as the test region will allow. Calculate the area of the test specimen and record to the nearest 0.1 square centimeter. Test results for any test specimen that is less than the ideal size will be normalized based on the area tested.

Insert the test specimen into the high sensitivity attachment such that the second and fourth pins from the left are above the test specimen, the first and third pins from the left are below the test specimen and the length of the test specimen is perpendicular to the pins. Ensure that the pins make contact with the test specimen but do not exert pressure on it. Measure the test specimen with a 15 degree deflection to the right and record the result to the nearest 1 Taber Stiffness Unit. Multiply the result by 0.01 (scaling multiplier for the SR Attachment+10 Unit Compensator) and record as Cuff Stiffness to the nearest 0.01 Taber Stiffness Unit. Normalize the result for any test specimen that was less than 3.81 cm×3.81 cm by dividing the result (in Taber Stiffness Units) by the specimen area (in square centimeters) and then multiply by 14.5 square centimeters (area of ideal sample size). Note that 1 Taber Stiffness Unit is equivalent to 1 gram centimeter. Report results for Cuff Stiffness to the nearest 0.01 g*cm.

In like fashion, repeat for a total of ten replicate test specimens (e.g. test specimens taken from both sides of 5 substantially similar absorbent articles). Calculate the arithmetic mean for Cuff Stiffness and report to the nearest 0.01 g*cm.

Whole Pad Stiffness

The stiffness of the core-containing region of an absorbent article is measured on a constant rate of extension tensile tester (a suitable instrument is the MTS Alliance using Testworks 4.0 Software, as available from MTS Systems Corp., Eden Prairie, MN) using a load cell for which the forces measured are within 1% to 99% of the limit of the cell. All testing is performed in a room controlled at 23° C.±3 C° and 50%±2% relative humidity and test samples are conditioned in this environment for at least 2 hours prior to testing.

The fixture used to measure core stiffness is depicted in FIGS. 7a and 7b. The bottom stationary fixture consists of a horizontal smooth-polished stainless steel platform 1001 which is 102.0 mm wide by 102.0 mm long by 6.35 mm thick. The platform has 18.75 mm diameter orifice 1002 at its center with a lap edge 1003 of that orifice having a 45 degree angle to a depth of 4.75 mm (i.e., the outer diameter of bevel is 28.25 mm). The fixture is constructed such that it has at least 20 mm of clearance underneath the platform. The platform 1001 has an adapter 1004 compatible with the mount of the tensile tester capable of securing the platform horizontally and orthogonal to the pull direction of the tensile tester. The upper fixture is a cylindrical plunger 1005 having an overall length of 70 mm with a diameter of 6.25 mm. The contact tip 1006 is a ball nose having a radius of 2.97 mm. The plunger has an adapter 1007 compatible with the mount on the load cell capable of securing the plunger orthogonal to the platform. Once assembled, the plunger is concentric with the orifice with equal clearance on all sides.

To prepare a test specimen, first obtain a test sample and remove it from any wrapper present. If folded, gently unfold it and smooth out any wrinkles. If present, remove the release paper to expose the adhesive on the garment facing side of the test sample. Lightly apply talc powder to the adhesive on the backsheet to mitigate tackiness. A 37.5 mm by 37.5 mm test specimen is cut from the center of the test region on the test sample in an area free of folds. The test region is preferably at the intersection of the longitudinal and lateral midpoints of the absorbent core, however the test specimen must contain the largest sampling of the absorbent core as possible. The edges of the test specimen must be parallel to the longitudinal and lateral axes of the test sample.

Set the gage length to 15.0 mm from the bottom contact tip 1006 of the plunger to the bottom surface of the platform 1001. Program the tensile tester as a compression test, to lower the crosshead at 50.0 cm per minute for 15.0 mm and record force (N) and displacement (mm) at a data rate of 400 Hz, and then return the crosshead to its original gage length.

Zero the crosshead and load cell. Position the test specimen, topsheet side facing up, centered underneath the plunger with its edges parallel and perpendicular with the edges of the platform 1001. Begin the test and collect force (N) and displacement (mm) data. Construct a graph of force (N) versus displacement (mm). Determine the maximum peak force (N) from the graph and record as Pad Stiffness to the nearest 0.01 N.

In like fashion, repeat the test for a total of five replicate test specimens obtained from 5 substantially similar test samples. Calculate the arithmetic mean for the peak force and report as Pad Stiffness to the nearest 0.01 N.

Basis Weight

The basis weight of a test specimen is the mass (in grams) per unit area (in square meters) of a single layer of material. The mass of the test specimen is cut to a known area, and the mass of the specimen is determined using an analytical balance accurate to 0.0001 grams. All measurements are performed in a laboratory maintained at 23° C.±2 C° and 50%±2% relative humidity and test specimens are conditioned in this environment for at least 2 hours prior to testing.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, near the longitudinal midpoint of the absorbent article. The test specimen must be as large as possible so that any inherent material variability is accounted for. Basis weight is measured on a single layer of material. Thus, if the test specimen consists of multiple layers or is in a folded state when attached to the absorbent article, unfold the test specimen such that only one layer of material is analyzed.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens (e.g. test specimens taken from both sides of 5 substantially similar absorbent articles). Calculate the arithmetic mean for Basis Weight and report to the nearest 0.01 grams/square meter.

Cuff Thickness

The thickness of a test specimen is measured as the distance between a reference platform on which the specimen rests and a pressure foot that exerts a specified amount of pressure onto the specimen over a specified amount of time. All measurements are performed in a laboratory maintained at 23° C.±2 C° and 50%±2% relative humidity and test specimens are conditioned in this environment for at least 2 hours prior to testing.

Thickness is measured with a manually-operated micrometer equipped with a pressure foot capable of exerting a steady pressure of 3.5 kPa±0.01 kPa onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 6.85 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, near the longitudinal midpoint of the absorbent article. The test specimen must be larger than the pressure foot, and its presentation in the absorbent article must be represented during this test (e.g. if folded to give multiple layers, the thickness of all layers is measured).

To measure thickness, first zero the micrometer against the horizontal flat reference platform. Place the test specimen on the platform with the test location centered below the pressure foot. Gently lower the pressure foot with a descent rate of 1.0 mm±0.1 mm per second until the full pressure is exerted onto the test specimen. Wait 5 seconds and then record the thickness of the test specimen to the nearest 0.01 mm. In like fashion, repeat for a total of ten replicate test specimens (e.g. test specimens taken from both sides of 5 substantially similar absorbent articles). Calculate the arithmetic mean for all thickness measurements and report as Cuff Thickness to the nearest 0.01 mm.

EXAMPLES

Inventive Sample ("IS") 1 is used as the "control" in each of the tests described below and has the following basic construction, corresponding to the absorbent article illustrated in FIGS. 1, 4 and 5(a).

TABLE II

| Layer | Composition | Basis Weight |
|---|---|---|
| Topsheet | Bi-component non-woven | 18 gsm |
| Secondary Topsheet | Carded non-woven | 55 gsm |
| Absorbent Core | Pulp with AGM (Absorbent Gelling Material) | 310 gsm |
| Impermeable Backsheet | Polymer Film | 12 gsm |

IS 1 further has non-elasticated cuffs with the following construction, best illustrated in FIG. 5(a). The cuffs of Inventive Sample (IS) 1 are formed of spunbond meltblown spunbond (SMS) material, having a basis weight of 15 gsm, a cuff stiffness of 0.09 g*cm and cuff thickness of 0.25 mm. As shown in FIG. 4, the cuffs are attached at the longitudinal edges of the absorbent article, extending from the front of the absorbent article to the rear. Each cuff is formed of a single piece of material that is folded at a distal end of the cuff to form two layers of material, the ends of which are crimped to the topsheet at a periphery of the absorbent article. In a central section, shown in FIG. 4 and cross-section shown in FIG. 5(a). x, the absorbent article has a total width of 81 mm, and the absorbent core has a width of 59 mm. The cuffs have a width of 8.7 mm, measured from the proximal end to the distal end of the respective cuffs along the lateral centerpoint. The attachment strip has a width of 6.8 mm. An outer edge of the core in the central section is located a distance of 4.2 mm away from the inner edge of the attachment point and the distal end of each cuff extends a distance of 4.5 mm over the respective edge of the absorbent core (thus in total, 15% of the total core width is covered).

Each other sample tested features some variation vs Inventive Sample 1, as follows.

TABLE III

| | Variation vs Inventive Sample 1 | Inventive Sample 1 Relevant Information |
|---|---|---|
| Comparative Example 1 | NO CUFFS | Cuffs as described above |
| Comparative Example 2 | Width of cuff from proximal end to distal end is 3 mm | 8.7 mm |
| Comparative Example 3 | Folded layer with cuff stiffness of 0.034 g*cm | Folded layer with cuff stiffness of 0.09 g*cm |
| Inventive Sample 2 | Single layer with cuff stiffness of 0.43 g*cm | proximal end of cuff coterminous with longitudinal edge of chassis |
| Inventive Sample 3 | Absorbent article not folded post manufacture and before use | Tri-folded |

TABLE IV

| Sample | CD Run-off (%) |
|---|---|
| CE 1 | 27 |
| CE 2 | 20 |
| CE 3 | 23 |
| IS 1 | 6 |
| IS 2 | 14 |

CD Run-off provides an indication of how the cuffs may perform when an absorbent article is in use. In this respect, CD Run-off provides a measure of the % of exudate that runs off the side of an absorbent article. In all cases, a % of exudate is absorbed in the absorbent article (all comparative examples and inventive samples have the same chassis & absorbent core structure, the only difference is in the presence of or structure of the cuffs). In summary:
 i. CE 1 (no cuffs) is the control and indicates that without cuffs, 27% of exudates run laterally off the surface of the topsheet.
 ii. CE 2 has a relatively short pleat (3 mm vs 8.7 mm in inventive samples 1 and 2), showing that the length of the cuffs has an impact on the performance of the pleats in retaining exudates on the absorbent article long enough for them to be absorbed.
 iii. CE 3 has a cuff that is less stiff than IS 1. From the CD run-off data, it can be seen that the stiffer cuffs of IS 1 perform better in retaining exudates on the absorbent article.
 iv. It can further be seen when comparing IS 2 and IS 1 that having multiple layers of folded material performs better with respect to CD run-off of exudates than a single layer of material.

TABLE V

| Sample | Stand up Cuff Height (mm) |
|---|---|
| CE 2 | 0.09 |
| IS 1 | 2.35 |
| IS 2 | 2.30 |
| IS 3 | 1.97 |

The stand-up cuff height provides a measure of how the cuffs stand-up relative to the topsheet, thus providing an indication of how well they separate from the topsheet and how much of a barrier they may provide. In summary:

i. CE 2 has a cuff length (measured from proximal end to distal end) of 3 mm. All inventive samples have cuffs of length 8.9 mm and it can be seen from the above that the longer cuff length leads to better stand-up cuff height.
ii. IS 2 is a stiffer material than IS 1 and this translates to better stand-up cuff height. Although, as seen above, the multiple layers of IS 1 contribute more to retaining exudates on the absorbent article.
iii. IS 3 is not tri-folded prior to use, whereas IS 1 is. From the results, it can be seen that cuffs on the absorbent article that is tri-folded prior to use stand-up more relative to the topsheet.

The whole pad stiffness can be about 331 gf. However, forms are contemplated where the whole pad stiffness is in a range of from about 150 to 500 gf, from about 170 to about 450 gf, from about 200 to about 400 gf, from about 250 to about 350 gf, specifically reciting all values within these ranges and any ranges created thereby. It is worth noting however, that too high of a whole pad stiffness value can negatively impact conformance of the pad to the body, thereby leading to comfort issues. Similarly, too low of an overall pad stiffness value can similarly impact comfort as well as application of the pad to a user's underwear. For example, too low of a pad stiffness value means that the resulting pad lacks structural integrity and may be flimsy during application.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular forms of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline, the absorbent article comprising:
   a) a chassis comprising a topsheet and backsheet;
   b) an absorbent core disposed between the topsheet and backsheet, wherein a joining means is disposed on a garment-facing surface of the backsheet;
   c) first and second non-elasticated cuffs provided on a body facing surface of the absorbent article on opposite sides of the longitudinal centerline, each of the cuffs having a proximal end attached to the chassis in an attachment area and a distal end extending towards the longitudinal centerline, wherein the width of each of the cuffs measured between the proximal end and the distal end is at least 3 mm, wherein each of the cuffs is formed of a single layer of material folded at the distal end to form at least two layers, wherein each of the cuffs has a cuff stiffness of at least 0.04 g*cm, wherein the joining means is disposed inboard of the attachment area,
   wherein the absorbent article has a whole pad stiffness of at least 331 gf, wherein the distal end of each of the first and second non-elasticated cuffs extends towards the longitudinal centerline to cover from 10% to 70% of the absorbent core and at least 30% of the absorbent core remains exposed, and
   wherein the first and second non-elasticized cuff have a stand up cuff height of greater than 2 mm.

2. An absorbent article having a longitudinal centerline, the absorbent article comprising:
   a) a chassis comprising a topsheet and backsheet;
   b) an absorbent core disposed between the topsheet and backsheet, wherein a joining means is disposed on a garment-facing surface of the backsheet;
   c) first and second non-elasticated cuffs provided on a body facing surface of the absorbent article on opposite sides of the longitudinal centerline, each of the cuffs having a proximal end attached to the chassis and a distal end extending towards the longitudinal centerline, wherein the width of the cuff measured between the proximal end and the distal end varies along the longitudinal centerline and is at least 3 mm, and wherein each of the cuffs has a cuff stiffness of at least 0.04 g*cm, wherein the joining means and the proximal end of the cuff attached to the chassis do not overlap, and
   wherein the first and second non-elasticized cuff have a stand up cuff height of greater than 2 mm.

3. An absorbent article according to claim 2, wherein at least one of the first and second cuffs comprises more than one layer of material.

4. An absorbent article according to claim 2, wherein the first and second cuffs are formed of a single layer of material folded at the distal end to form cuffs having multiple layers.

5. An absorbent article according to claim 2, wherein each layer of material is attached to the chassis.

6. An absorbent article according to claim 2, wherein a proximal end of the first and second cuffs is coterminous with a longitudinal edge of the chassis.

7. An absorbent article according to claim 2, wherein the distal end of the first and second cuffs extends over the absorbent core by at least 0.5 mm.

8. An absorbent article according to claim 2, wherein the absorbent article has a whole pad stiffness of at least 331 gf.

9. An absorbent article according to claim 2, wherein the first and second cuffs are crimped and/or glued to a topsheet of the absorbent article along an attachment strip.

10. An absorbent article as claimed in claim 9, wherein the attachment strip has a width of at least 1 mm.

11. An absorbent article according to claim 10, wherein the joining means and the attachment strip do not overlap in a central section of the absorbent article.

12. An absorbent article according to claim 11, wherein the joining means are located inboard of the attachment strip in at least a central section of the absorbent article.

13. An absorbent article according to claim 2, wherein at a front and/or rear end of the absorbent article, the distal ends of the first and second cuffs are attached to the chassis.

14. An absorbent article according to claim 2, wherein the first and second cuffs are formed of the same material as the topsheet.

15. An absorbent article according to claim 14, wherein the first and second cuffs and topsheet are formed from a single sheet of material.

16. An absorbent article according to claim 2, wherein the distance between the distal ends of the first and second cuffs is at least 30% of the width at the narrowest section of the absorbent core.

17. An absorbent article according to claim 2, wherein the first and second cuffs are formed of hydrophobic material.

18. An absorbent article according to claim 2, wherein a topsheet facing surface of the first and second cuffs lies flush with the topsheet prior to use of the absorbent article, and wherein during use the distal ends of the first and second cuffs stand-up relative to the topsheet in at least a central section of the absorbent article.

19. The absorbent article according to claim 1, wherein the absorbent article comprises fold lines extending in a direction substantially parallel to the longitudinal centerline, and wherein the fold lines predispose the distal ends of the cuffs to separate from the topsheet in a central region between the fold lines.

* * * * *